(12) United States Patent
Gonzalez-Hernandez

(10) Patent No.: US 8,690,916 B2
(45) Date of Patent: Apr. 8, 2014

(54) SOFT TISSUE ATTACHMENT SYSTEM AND CLIP

(71) Applicant: Eduardo Gonzalez-Hernandez, Miami, FL (US)

(72) Inventor: Eduardo Gonzalez-Hernandez, Miami, FL (US)

(*) Notice: Subject to any disclaimer, the term of this patent is extended or adjusted under 35 U.S.C. 154(b) by 0 days.

(21) Appl. No.: 13/925,964

(22) Filed: Jun. 25, 2013

(65) Prior Publication Data

US 2013/0289627 A1    Oct. 31, 2013

Related U.S. Application Data

(60) Division of application No. 13/439,717, filed on Apr. 4, 2012, now Pat. No. 8,469,999, which is a continuation of application No. 12/121,269, filed on May 15, 2008, now abandoned.

(60) Provisional application No. 61/045,860, filed on Apr. 17, 2008.

(51) Int. Cl.
*A61B 17/04* (2006.01)

(52) U.S. Cl.
USPC .......................................... 606/232

(58) Field of Classification Search
USPC .................... 606/139–145, 228, 232, 280
See application file for complete search history.

(56) References Cited

U.S. PATENT DOCUMENTS

| | | | |
|---|---|---|---|
| 1,950,799 A | 3/1934 | Jones | |
| 2,500,370 A | 3/1950 | McKibbin | |
| 2,555,291 A | 5/1951 | Poupitch | |
| 2,875,663 A | 3/1959 | Wieber | |
| 3,489,143 A | 1/1970 | Halloran | |
| 3,552,389 A | 1/1971 | Allgower et al. | |
| 3,579,831 A | 5/1971 | Stevens et al. | |
| 3,716,050 A | 2/1973 | Johnston | |
| 3,791,380 A | 2/1974 | Dawidowski | |
| 3,900,025 A | 8/1975 | Barnes, Jr. | |
| 4,263,904 A | 4/1981 | Judet | |
| 4,535,768 A | 8/1985 | Hourahane et al. | |
| 4,683,878 A | 8/1987 | Carter | |
| 4,733,654 A | 3/1988 | Marino | |
| 4,776,330 A | 10/1988 | Chapman et al. | |

(Continued)

FOREIGN PATENT DOCUMENTS

| | | |
|---|---|---|
| DE | 86 28 766 U1 | 12/1986 |
| DE | 89 07 443 U1 | 9/1989 |

(Continued)

OTHER PUBLICATIONS

U.S. Appl. No. 10/993,723, filed Nov. 2004, Gonzalez-Hernandez.

(Continued)

*Primary Examiner* — Sameh Boles
(74) *Attorney, Agent, or Firm* — Martin & Ferraro, LLP

(57) ABSTRACT

A suture attachment clip and method for assisting in the attachment or re-attachment of soft tissue to bone. The clip generally comprises a head having a shape suitable for allowing the passage of a suture during attachment of soft tissue to bone. One or more clips can be secured to a bone plate through a variety of means, including a snap configuration, a screw configuration, and a bendable prong configuration. The clip can also be continuous with an adjacent clip, thus forming a multi-clip assembly that can either be secured to a bone plate or secured directly to a bone without a bone plate.

4 Claims, 10 Drawing Sheets

(56) References Cited

U.S. PATENT DOCUMENTS

| | | | |
|---|---|---|---|
| 4,790,302 A | 12/1988 | Colwill et al. | |
| 4,794,919 A | 1/1989 | Nilsson | |
| 4,838,264 A | 6/1989 | Bremer et al. | |
| 4,858,602 A | 8/1989 | Seidel et al. | |
| 4,870,957 A * | 10/1989 | Goble et al. | 623/13.12 |
| 5,003,969 A | 4/1991 | Azer et al. | |
| 5,015,248 A | 5/1991 | Burstein et al. | |
| 5,041,113 A | 8/1991 | Biedermann et al. | |
| 5,041,114 A | 8/1991 | Chapman et al. | |
| 5,180,383 A | 1/1993 | Haydon | |
| 5,190,544 A | 3/1993 | Chapman et al. | |
| 5,324,291 A | 6/1994 | Ries et al. | |
| 5,356,410 A | 10/1994 | Pennig | |
| 5,364,399 A | 11/1994 | Lowery et al. | |
| 5,423,860 A | 6/1995 | Lizardi et al. | |
| 5,437,667 A | 8/1995 | Papierski et al. | |
| 5,443,516 A | 8/1995 | Albrektsson et al. | |
| 5,458,654 A | 10/1995 | Tepic | |
| 5,462,547 A | 10/1995 | Weigum | |
| 5,472,444 A | 12/1995 | Huebner et al. | |
| 5,505,734 A | 4/1996 | Caniggia et al. | |
| 5,578,035 A | 11/1996 | Lin | |
| 5,584,835 A | 12/1996 | Greenfield | |
| 5,586,985 A | 12/1996 | Putnam et al. | |
| 5,601,553 A | 2/1997 | Trebing et al. | |
| 5,620,449 A | 4/1997 | Faccioli et al. | |
| 5,658,287 A | 8/1997 | Hofmann et al. | |
| 5,665,088 A | 9/1997 | Gil et al. | |
| 5,674,222 A | 10/1997 | Berger et al. | |
| 5,676,667 A | 10/1997 | Hausman | |
| 5,681,311 A | 10/1997 | Foley et al. | |
| 5,709,686 A | 1/1998 | Talos et al. | |
| 5,749,872 A | 5/1998 | Kyle et al. | |
| 5,766,174 A | 6/1998 | Perry | |
| 5,776,194 A | 7/1998 | Mikol et al. | |
| 5,779,704 A | 7/1998 | Kim | |
| 5,785,712 A | 7/1998 | Runciman et al. | |
| 5,840,078 A | 11/1998 | Yerys | |
| 5,868,749 A | 2/1999 | Reed | |
| 5,931,839 A | 8/1999 | Medoff | |
| 5,976,139 A | 11/1999 | Bramlet | |
| 6,030,389 A | 2/2000 | Wagner et al. | |
| 6,096,040 A | 8/2000 | Esser | |
| 6,149,653 A | 11/2000 | Deslauriers | |
| 6,152,927 A | 11/2000 | Farris et al. | |
| 6,200,330 B1 | 3/2001 | Benderev et al. | |
| 6,206,881 B1 | 3/2001 | Frigg et al. | |
| D443,060 S | 5/2001 | Benirschke et al. | |
| 6,270,499 B1 | 8/2001 | Leu et al. | |
| D449,692 S | 10/2001 | Michelson | |
| 6,302,887 B1 | 10/2001 | Spranza et al. | |
| 6,331,179 B1 | 12/2001 | Freid et al. | |
| 6,348,052 B1 | 2/2002 | Sammarco | |
| 6,358,250 B1 | 3/2002 | Orbay | |
| 6,364,881 B1 | 4/2002 | Apgar et al. | |
| 6,364,882 B1 | 4/2002 | Orbay | |
| 6,379,359 B1 | 4/2002 | Dahners | |
| 6,398,783 B1 | 6/2002 | Michelson | |
| 6,406,478 B1 | 6/2002 | Kuo | |
| 6,409,768 B1 | 6/2002 | Tepic et al. | |
| 6,413,259 B1 | 7/2002 | Lyons et al. | |
| 6,440,135 B2 | 8/2002 | Orbay et al. | |
| 6,468,278 B1 | 10/2002 | Muckter | |
| 6,572,620 B1 | 6/2003 | Schon et al. | |
| 6,620,195 B2 | 9/2003 | Goble et al. | |
| 6,623,486 B1 | 9/2003 | Weaver et al. | |
| 6,663,669 B1 | 12/2003 | Reiley | |
| 6,669,701 B2 | 12/2003 | Steiner et al. | |
| 6,695,844 B2 | 2/2004 | Bramlet et al. | |
| 6,706,046 B2 | 3/2004 | Orbay et al. | |
| 6,712,820 B2 | 3/2004 | Orbay | |
| 6,719,759 B2 | 4/2004 | Wagner et al. | |
| 6,730,090 B2 | 5/2004 | Orbay et al. | |
| 6,776,781 B1 | 8/2004 | Uwaydah | |
| 6,863,671 B1 | 3/2005 | Strobel et al. | |
| 6,866,665 B2 | 3/2005 | Orbay | |
| 6,916,323 B2 | 7/2005 | Kitchens | |
| 6,945,973 B2 | 9/2005 | Bray | |
| 7,001,388 B2 | 2/2006 | Orbay et al. | |
| 7,063,701 B2 | 6/2006 | Michelson | |
| 7,128,744 B2 | 10/2006 | Weaver et al. | |
| D536,453 S | 2/2007 | Young et al. | |
| 7,220,246 B2 | 5/2007 | Raulerson et al. | |
| 7,229,445 B2 | 6/2007 | Hayeck et al. | |
| 7,235,079 B2 | 6/2007 | Jensen et al. | |
| 7,354,441 B2 | 4/2008 | Frigg | |
| 7,500,983 B1 | 3/2009 | Kaiser et al. | |
| 7,563,263 B2 | 7/2009 | Orbay et al. | |
| 7,582,107 B2 | 9/2009 | Trail et al. | |
| 7,591,823 B2 | 9/2009 | Tipirneni | |
| 7,604,657 B2 | 10/2009 | Orbay et al. | |
| 7,637,908 B1 | 12/2009 | Gonzalez-Hernandez | |
| 7,651,517 B2 | 1/2010 | Konieczynski et al. | |
| 7,655,029 B2 | 2/2010 | Niederberger et al. | |
| 7,695,472 B2 | 4/2010 | Young | |
| 7,722,653 B2 | 5/2010 | Young et al. | |
| 7,740,648 B2 | 6/2010 | Young et al. | |
| 7,744,638 B2 | 6/2010 | Orbay | |
| 7,776,076 B2 | 8/2010 | Grady, Jr. et al. | |
| 7,780,667 B2 | 8/2010 | Wantanabe et al. | |
| 7,780,710 B2 | 8/2010 | Orbay et al. | |
| 7,896,886 B2 | 3/2011 | Orbay et al. | |
| 7,909,859 B2 | 3/2011 | Mosca et al. | |
| 7,914,532 B2 | 3/2011 | Shaver et al. | |
| 7,927,341 B2 | 4/2011 | Orbay et al. | |
| 7,938,850 B2 | 5/2011 | Orbay et al. | |
| 7,951,176 B2 | 5/2011 | Grady et al. | |
| 7,951,178 B2 | 5/2011 | Jensen | |
| 7,955,364 B2 | 6/2011 | Ziolo et al. | |
| D643,121 S | 8/2011 | Milford et al. | |
| D646,785 S | 10/2011 | Milford | |
| 8,062,367 B2 | 11/2011 | Kirschman | |
| 8,100,953 B2 | 1/2012 | White et al. | |
| 8,182,485 B1 | 5/2012 | Gonzalez-Hernandez | |
| 8,361,075 B2 | 1/2013 | Gonzalez-Hernandez | |
| 8,469,999 B2 | 6/2013 | Gonzalez-Hernandez | |
| 8,574,234 B2 | 11/2013 | Gonzalez-Hernandez | |
| 2003/0135212 A1 | 7/2003 | Chow | |
| 2003/0135216 A1 | 7/2003 | Sevrain | |
| 2004/0097939 A1 | 5/2004 | Bonutti | |
| 2004/0193278 A1 | 9/2004 | Maroney et al. | |
| 2004/0210220 A1 | 10/2004 | Tornier | |
| 2005/0004574 A1 | 1/2005 | Muckter | |
| 2005/0015089 A1 | 1/2005 | Young et al. | |
| 2005/0021033 A1 | 1/2005 | Zeiler et al. | |
| 2005/0038513 A1 | 2/2005 | Michelson | |
| 2005/0085819 A1 | 4/2005 | Ellis et al. | |
| 2005/0240187 A1 | 10/2005 | Huebner et al. | |
| 2005/0267476 A1 | 12/2005 | Chervitz et al. | |
| 2005/0288681 A1 | 12/2005 | Klotz et al. | |
| 2006/0015072 A1 | 1/2006 | Raulerson | |
| 2006/0015101 A1 | 1/2006 | Warburton et al. | |
| 2006/0161156 A1 | 7/2006 | Orbay | |
| 2006/0217722 A1 | 9/2006 | Dutoit et al. | |
| 2006/0235400 A1 | 10/2006 | Schneider | |
| 2006/0241617 A1 | 10/2006 | Holloway et al. | |
| 2006/0264947 A1 | 11/2006 | Orbay et al. | |
| 2006/0264956 A1 | 11/2006 | Orbay et al. | |
| 2007/0005074 A1 | 1/2007 | Chudik | |
| 2007/0016205 A1 | 1/2007 | Buetter et al. | |
| 2007/0083207 A1 | 4/2007 | Ziolo et al. | |
| 2007/0123880 A1 | 5/2007 | Medoff | |
| 2007/0123885 A1 | 5/2007 | Kirschman | |
| 2007/0162015 A1 | 7/2007 | Winquist et al. | |
| 2007/0167953 A1 | 7/2007 | Prien et al. | |
| 2007/0233114 A1 | 10/2007 | Bouman | |
| 2007/0233115 A1 | 10/2007 | Sixto et al. | |
| 2008/0015593 A1 | 1/2008 | Pfefferle et al. | |
| 2008/0045960 A1 | 2/2008 | Bruecker et al. | |
| 2008/0091203 A1 | 4/2008 | Warburton et al. | |
| 2008/0132955 A1 | 6/2008 | Frigg | |
| 2008/0140130 A1 | 6/2008 | Chan et al. | |
| 2008/0154311 A1 | 6/2008 | Staeubli | |
| 2008/0161853 A1 | 7/2008 | Arnold et al. | |

(56) References Cited

U.S. PATENT DOCUMENTS

| | | |
|---|---|---|
| 2008/0161860 A1 | 7/2008 | Ahrens et al. |
| 2008/0161863 A1 | 7/2008 | Arnold et al. |
| 2008/0221577 A1 | 9/2008 | Elghazaly |
| 2008/0234749 A1 | 9/2008 | Forstein |
| 2008/0234752 A1 | 9/2008 | Dahners |
| 2008/0249572 A1 | 10/2008 | Tandon |
| 2009/0012571 A1 | 1/2009 | Perrow et al. |
| 2009/0024173 A1 | 1/2009 | Reis, Jr. |
| 2009/0048681 A1 | 2/2009 | Vlachos |
| 2009/0076554 A1 | 3/2009 | Huebner et al. |
| 2009/0105838 A1 | 4/2009 | Russo et al. |
| 2009/0171399 A1 | 7/2009 | White et al. |
| 2009/0192550 A1 | 7/2009 | Leung et al. |
| 2009/0216270 A1 | 8/2009 | Humphrey |
| 2009/0228010 A1 | 9/2009 | Gonzalez-Hernandez et al. |
| 2009/0254089 A1 | 10/2009 | Tipirneni et al. |
| 2009/0264936 A1 | 10/2009 | Gonzalez-Hernandez |
| 2009/0275987 A1 | 11/2009 | Graham et al. |
| 2009/0275991 A1 | 11/2009 | Medoff |
| 2009/0281578 A1 | 11/2009 | Spencer |
| 2009/0312760 A1 | 12/2009 | Forstein et al. |
| 2009/0312802 A1 | 12/2009 | Dasilva |
| 2009/0326591 A1 | 12/2009 | Spencer, Jr. |
| 2010/0145339 A1 | 6/2010 | Steffen |
| 2010/0262194 A1 | 10/2010 | Wagner et al. |
| 2010/0324602 A1 | 12/2010 | Huebner et al. |
| 2010/0331844 A1 | 12/2010 | Ellis et al. |
| 2011/0152943 A1 | 6/2011 | Gonzalez-Hernandez |
| 2012/0083848 A1 | 4/2012 | Gonzalez-Hernandez |
| 2012/0109322 A1 | 5/2012 | Gonzalez-Hernandez |
| 2012/0197308 A1 | 8/2012 | Gonzalez-Hernandez |
| 2012/0226321 A1 | 9/2012 | Gonzalez-Hernandez |
| 2012/0226322 A1 | 9/2012 | Gonzalez-Hernandez |
| 2012/0226323 A1 | 9/2012 | Gonzalez-Hernandez |
| 2013/0116734 A1 | 5/2013 | Gonzalez-Hernandez |

FOREIGN PATENT DOCUMENTS

| | | |
|---|---|---|
| DE | 43 43 117 A1 | 6/1995 |
| DE | 198 57 279 A1 | 6/2000 |
| DE | 299 07 161 U1 | 8/2000 |
| EP | 0 551 588 A1 | 11/1992 |
| EP | 1 132 052 A2 | 9/2001 |
| EP | 1 468 655 A2 | 10/2004 |
| FR | 2 606 268 A1 | 5/1988 |
| FR | 2 680 673 A1 | 3/1993 |
| JP | 4-138152 A | 5/1992 |
| WO | WO 99/38448 A1 | 8/1999 |
| WO | WO 2005/037117 A1 | 4/2005 |
| WO | WO 2008/007194 A2 | 1/2008 |
| WO | WO 2008/007196 A2 | 1/2008 |

OTHER PUBLICATIONS

U.S. Appl. No. 11/079,350, filed Mar. 2005, Gonzalez-Hernandez.
U.S. Appl. No. 11/366,676, filed Mar. 2006, Gonzalez-Hernandez.
U.S. Appl. No. 11/493,122, filed Jul. 2006, Gonzalez-Hernandez.
U.S. Appl. No. 11/526,331, filed Sep. 2006, Gonzalez-Hernandez.
U.S. Appl. No. 11/707,775, filed Feb. 2007, Gonzalez-Hernandez.
U.S. Appl. No. 13/663,129, filed Oct. 2012, Gonzalez-Hernandez.
U.S. Appl. No. 13/663,209, filed Oct. 2012, Gonzalez-Hernandez.
ACUMED; The Mayo Clinic Congruent Elbow Plates (catalog); 2003; 19 pages.
ACUMED; The Mayo Clinic Congruent Elbow Plate System (catalog); Apr. 2006; 20 pages.
Christie, J., C.R. Howie and P.C. Armour, *Fixation of displaced subcapital femoral fractures. Compression screw fixation versus double divergent pins. J Bone Joint Surq* [*Br*] 1988; 70-B: 199-201.
Cross, W.M. et al., "Achieving stable fixation: biomechanical designs for fracture healing," AAOS Now (2008) 3 pages.
Guha, AR, et al.; "A New Technique of Fixation of Radial Head Fractures Using a Modified Tubular Plate," Journal of Postgraduate Medicine; Jul. 2004; vol. 50, Issue 2; pp. 113-114; Accessed Aug. 6, 2008 at: http://www.jpgmonline.com/article.asp?issn=0022-3859;year=2004;volume=50;issue=2;spage=113;epage=114;aulast=Guha.
Hand Innovations, LLC; DVR ANATOMIC, Volar Plating System; 2007; 4 pages.
Lakatos, R. et al.; "General principles of internal fixation"; eMedicine; Aug. 2006; 51 pages.
"MIS Technique," published by Zimmer®, 1 page, prior to Nov. 19, 2004.
Postak, Paul D.; "Biomechanical Properties of Fixed-Angle Volar Distal Radius Plates Under Dynamic Loading;" 2007; 6 pages.
Robert, III, K.Q., R. Chandler, R,V, Barratta, K.A. Thomas and M.B. Harris, *The effect of divergent screw placement on the initial strength of plate-to-bone fixation. J Trauma*. Dec. 2003;55(6):1139-44.
Synthes, "Large Fragment LCP Instrument and Implant Set;" technique guide; 2003; 31 pages.
Synthes; Locking Compression Plate (LCP) System (brochure); 2003; 6 pages.
Synthes, "Locking Compression Plate (LCP) System. Locking screw technology and conventional plating in one system;" 2003; 6 pages.
Synthes; Locking Compression Plate (LCP) System (brochure); Jan. 2007; 6 pages.
Synthes; Modular Mini Fragment LCP System (brochure); 2007; 12 pages.
Synthes; Small Fragment Locking Compression Plate (LCP) System (brochure); 2002; 43 pages.
Written Opinion of the International Searching Authority; International Application No. PCT/US2009/036211; Sep. 23, 2010; 8 pages.
"Zimmer® Universal Locking System," The Journal of Bone and Joint Surgery, vol. 89, No. 7, Jul. 2007, 1 page.
Zimmer, Inc. "Zimmer® Universal Locking System," brochure (2006), 4 pages.
Zimmer, Inc. "Zimmer Holdings to Launch Innovative Locking Plate System at Orthopaedic Trauma Association Meeting," Sep. 14, 2006; 3 pages.
Zimmer; Zimmer Periarticular Plating System-Low-Profile Fixation (catalog); 2003; 8 pages.

\* cited by examiner

SOFT TISSUE ATTACHMENT SYSTEM AND CLIP

BACKGROUND OF THE INVENTION

The present application is a divisional of U.S. application Ser. No. 13/439,717, filed Apr. 4, 2012 (now U.S. Pat. No. 8,469,999); which is a continuation of U.S. application Ser. No. 12/121,269, filed May 15, 2008 (now abandoned); which claims the benefit of U.S. Provisional Application No. 61/045,860, filed on Apr. 17, 2008; all of which are incorporated by reference herein.

FIELD OF THE INVENTION

The present invention relates to orthopedic devices used in the reattachment of soft tissue to bone in acute injuries or reconstructive procedures.

DESCRIPTION OF THE PRIOR ART

The present device and method provides a significant improvement for soft tissue attachment or reattachment to bone in acute injury or in reconstructive procedures. The various embodiments of the present invention can be used in conjunction with bone plates or by itself.

Musculoskeletal injuries constitute combinations of bone and soft tissue injury. As such, bone fractures frequently have associated tendon or ligament tears. Fractures around joints—know in the art as periarticular fractures—are classic examples of combined bone and tendon, or bone and ligament injuries. Existing plate systems utilized in orthopaedic surgical procedures, such as fracture fixation or reconstruction procedures, provide limited options for incorporating additional soft tissue anchoring into the plate. In most instances the plates designed for use in periarticular fracture procedures will have a few small orifices for the passage of a curved surgical needle. A torn or avulsed tendon can be reattached to the bone at the time of fracture fixation through the small orifices on the plates. Often, the small amount and small size of the orifices on the plate are not sufficient to repair significant soft tissue components. In addition, it is often very difficult to pass a needle, curved or straight, through these orifices once the plate has been screwed to the bone. Accordingly, existing bone plates provide limited options for soft tissue reattachment.

While the clinical success of bone anchors for the reattachment of tendon or ligament in musculoskeletal reconstruction is well documented, most existing bone anchors fail where the bone is very soft—as, or example, in severe osteopenia—or where the bone is very fragmented—as, for example, in fractures with severe bone fragmentation or comminution. In these instances, traditional bone anchors are inadequate for the reattachment of tendons and ligaments to bone.

It is therefore an object of the present invention to broaden the usefulness of bone plates by introducing additional features to plate design and fabrication that facilitate the reattachment of soft tissue, tendons, and ligaments to bone. The present invention has applications in fracture situations, and reconstructive procedures alike.

It is a further object of the present invention to provide a means of soft tissue reattachment or attachment to bone that can be used by itself without a bone plate; specifically, when other traditional methods, such as bone anchors, will not provide sufficient strength for repair.

SUMMARY OF THE INVENTION

The present invention generally comprises a suture attachment clip having various embodiments which provide multiple options for soft tissue repair to a bone structure.

In one embodiment of the present invention, the suture attachment clip comprises a head suitably shaped to allow the passage of a suture during the attachment of soft tissue to bone. A plurality of individual clips can attach to a bone plate by snapping the respective clips into corresponding receiving orifices on the bone plate, preferably located on the side of the bone plate. The clips can be attached to the bone plate at the time of manufacture or at the time of surgery.

In another embodiment of the present invention, the plurality of individual clips are attached to the bone plate by screwing each respective clip into a corresponding receiving orifice on the bone plate, preferably located on the side of the bone plate and preferably threaded internally. The clips can be screwed into the bone plate at the time of manufacture or at the time of surgery.

In yet another embodiment of the present invention, the plurality of individual clips are attached to a bone plate by inserting a free end of each respective clip through a corresponding pair of receiving orifices in the bone plate, preferably located on the side of the bone plate. The free ends of the clip are then bent through a corresponding pair of exit orifices on the bone plate, wherein the clip is fixed in place. In this embodiment, a clip can be designed and manufactured specifically to fit an existing bone plate's orifices, or alternatively, the bone plate and clip can be simultaneously and compatibly designed and manufactured. Each clip has a head suitably shaped to allow the passage of a suture during the repair of soft tissue to bone. The clips can be attached to the bone plate at the time of manufacture or at the time of the actual surgery.

In yet another embodiment of the present invention, the terminal end of one suture attachment clip is continuous with the terminal end of an adjacent suture attachment clip, thus forming a single multi-clip assembly. Each clip of the multi-clip assembly has a head suitably shaped to allow the passage of a suture during the attachment of soft tissue to bone. The multi-clip assembly attaches to the bone plate by snapping the multi-clip assembly to corresponding receiving channels on the bone plate. The receiving channels are preferably located on the undersurface of the bone plate. To further secure the multi-clip assembly to the bone plate, the multi-clip assembly could alternatively be fastened to the bone plate by locking screws or fasteners. Depending on the fastening method used, the multi-clip assembly can be attached to the bone plate at the time of manufacture or at the time of the actual surgery.

The multi-clip assembly can also be used without attachment to a bone plate. In this embodiment of the present invention, the multi-clip assembly is fastened to the bone with standard bone screws or fasteners through a plurality of eyelets positioned at various points on the multi-clip assembly.

These and other objects of the present invention will be apparent from review of the following specification and the accompanying drawings.

DETAILED DESCRIPTION OF THE PREFERRED EMBODIMENT

Figure 1:
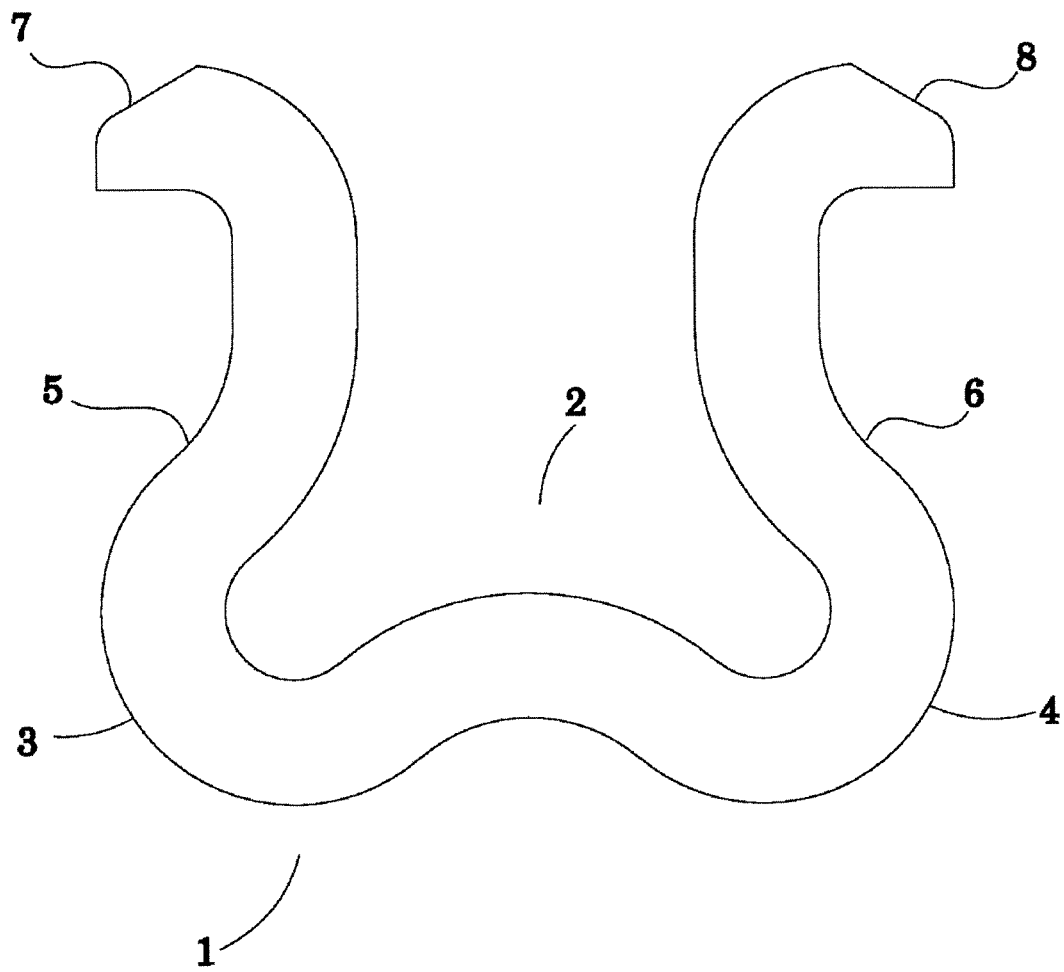
FIG. 1 illustrates a top perspective view of an individual clip with a snap configuration.

As shown in FIG. 1, in one embodiment of the present invention, the suture attachment clip 1 comprises a head 2 suitably shaped to allow the passage of a suture during the attachment of soft tissue to bone. In this embodiment, the head 2 preferably has a first and second lobe 3 and 4. In a preferred embodiment of the present invention, the first and second lobes 3 and 4 are symmetrical with respect to one another. In a preferred embodiment of the present invention, first and second lobes 3 and 4 are continuous with first and second prongs 5 and 6 wherein first prong 5 has a first outwardly protruding terminal end 7 and second prong 6 has a second outwardly protruding terminal end 8. Preferably, the head 2, prongs 5 and 6, and terminal ends 7 and 8 form an inverse-omega shape when clip 1 is viewed from the top perspective depicted in FIG. 1.

Figure 2:
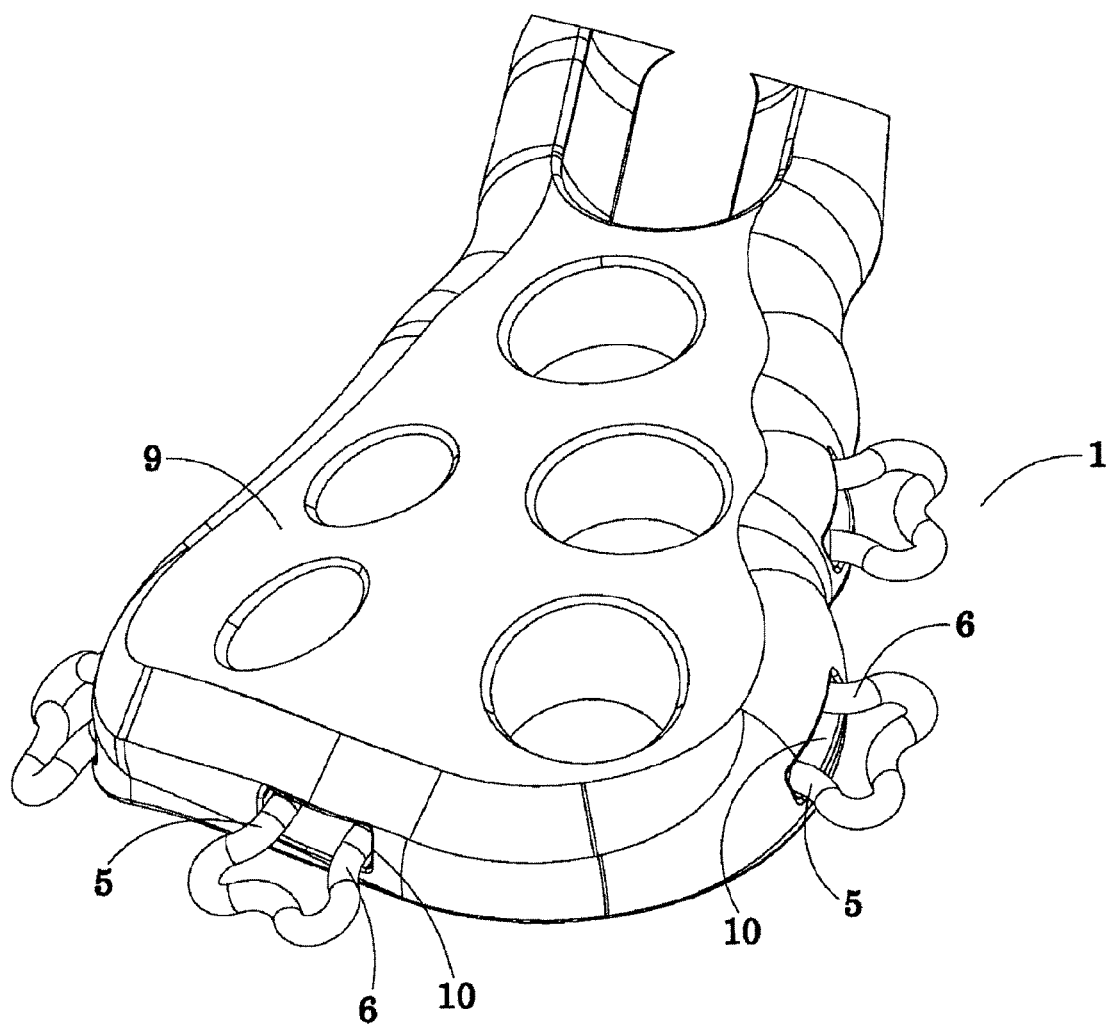
FIG. 2 illustrates a plurality of individual clips with snap configurations attached to a bone plate.

As shown in FIG. 2, a plurality of individual clips 1 can attach to a bone plate 9 by snapping prongs 5 and 6 of each respective clip 1 into a corresponding receiving orifice 10 on the bone plate 9. The receiving orifice 10 is preferably located on the edge of the bone plate 9. In this snapping configuration, pressure is applied to the prongs 5 and 6 so that the prongs are squeezed toward one another until each terminal end 7 and 8 can pass through the receiving orifice 10. When terminal ends 7 and 8 have sufficiently passed through the receiving orifice 10, pressure on the prongs 5 and 6 is released so that the prongs contact the edges of the receiving orifice 10, thereby securing the clip 1 to the bone plate 9. On or more clips 1 can be attached to the bone plate at the time of manufacture or at the time of surgery.

Figure 3:
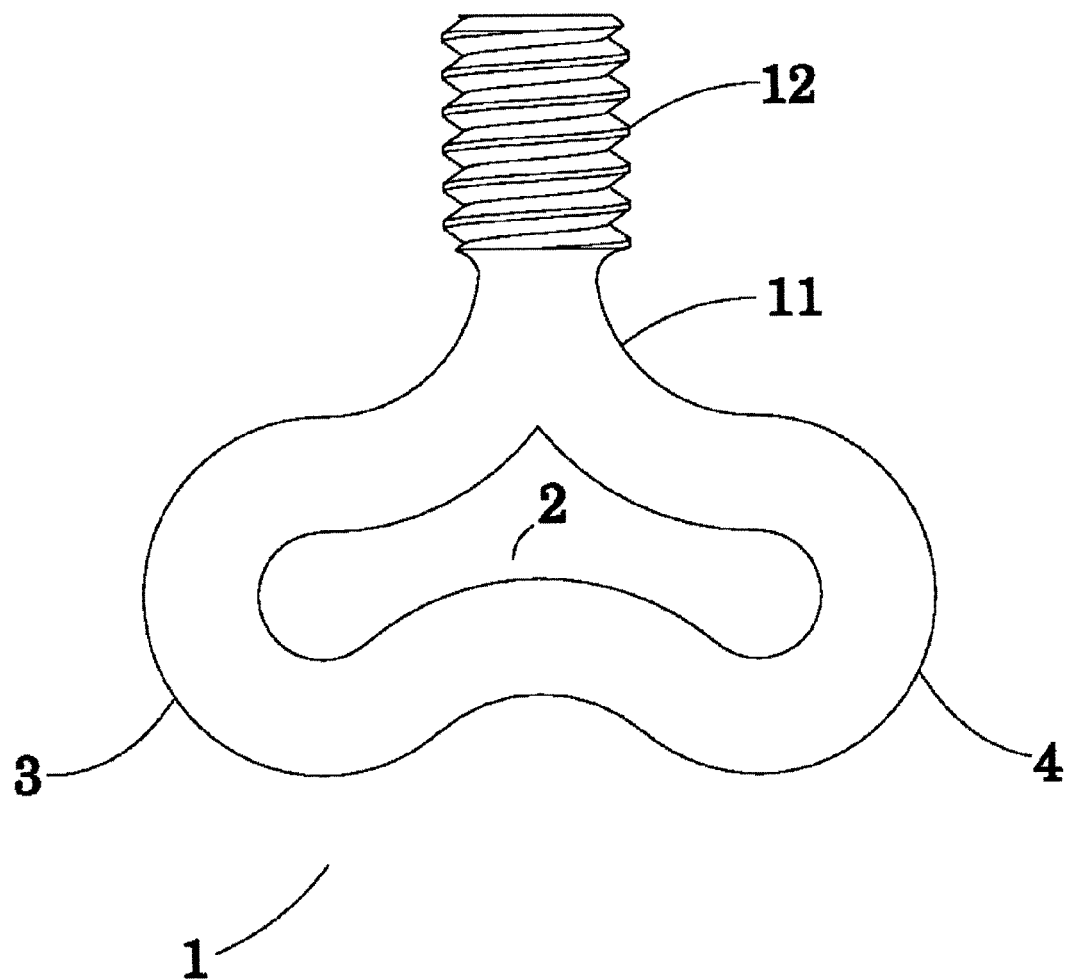
FIG. 3 illustrates a top perspective view of an individual clip with a threaded screw configuration.

As shown in FIG. 3, in another embodiment of the present invention, the suture attachment clip 1 comprises a head 2 suitably shaped to allow the passage of a suture during the attachment of soft tissue to bone. In this embodiment, the head 2 preferably has a first and second lobe 3 and 4 which fuse into a single prong 11. In a preferred embodiment of the present invention, the first and second lobes 3 and 4 are symmetrical with respect to one another. In a preferred embodiment of the present invention, single prong 11 has external threading 12.

Figure 4:
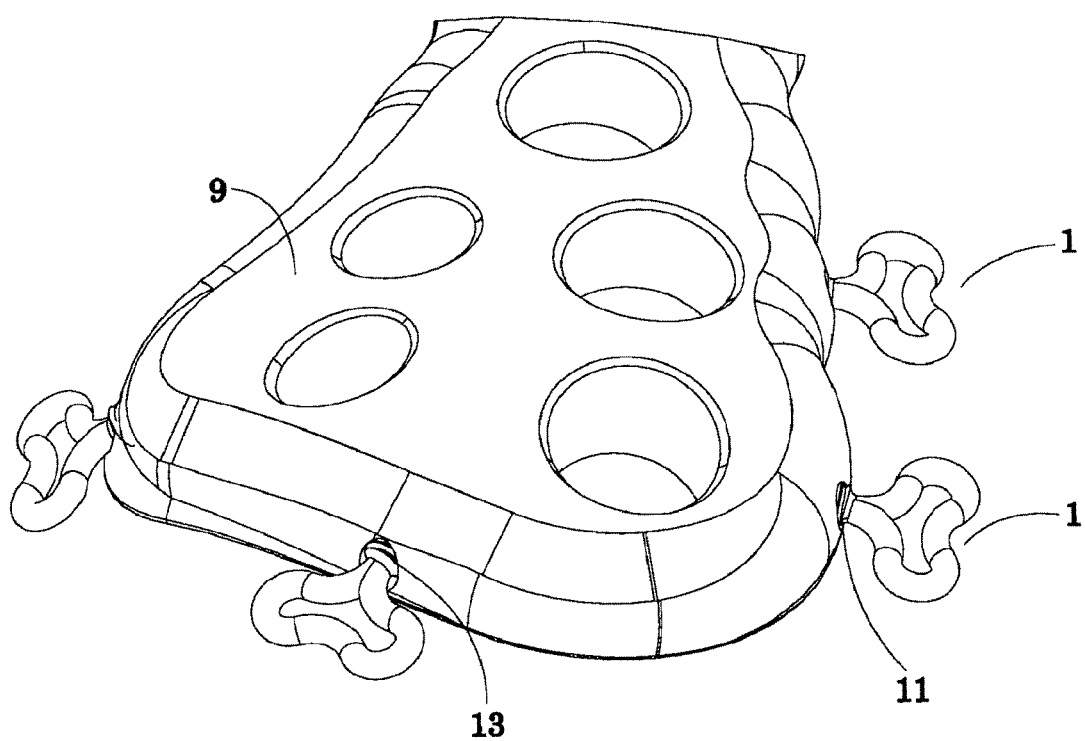
FIG. 4 illustrates a plurality of individual clips with threaded screw configurations attached to a bone plate.

As shown in FIG. 4, in the threaded screw configuration of the present invention, a plurality of individual clips 1 are attached to a bone plate 9 by screwing the single prong 11 of each respective clip 1 into a corresponding receiving orifice 13 on the bone plate 9, thereby securing the clip 1 to the bone plate 9. The receiving orifice 13 is preferably located on the edge of the bone plate 9 and is preferably threaded internally.

On or more clips 1 can be screwed into the bone plate at the time of manufacture or at the time of surgery.

Figure 5:
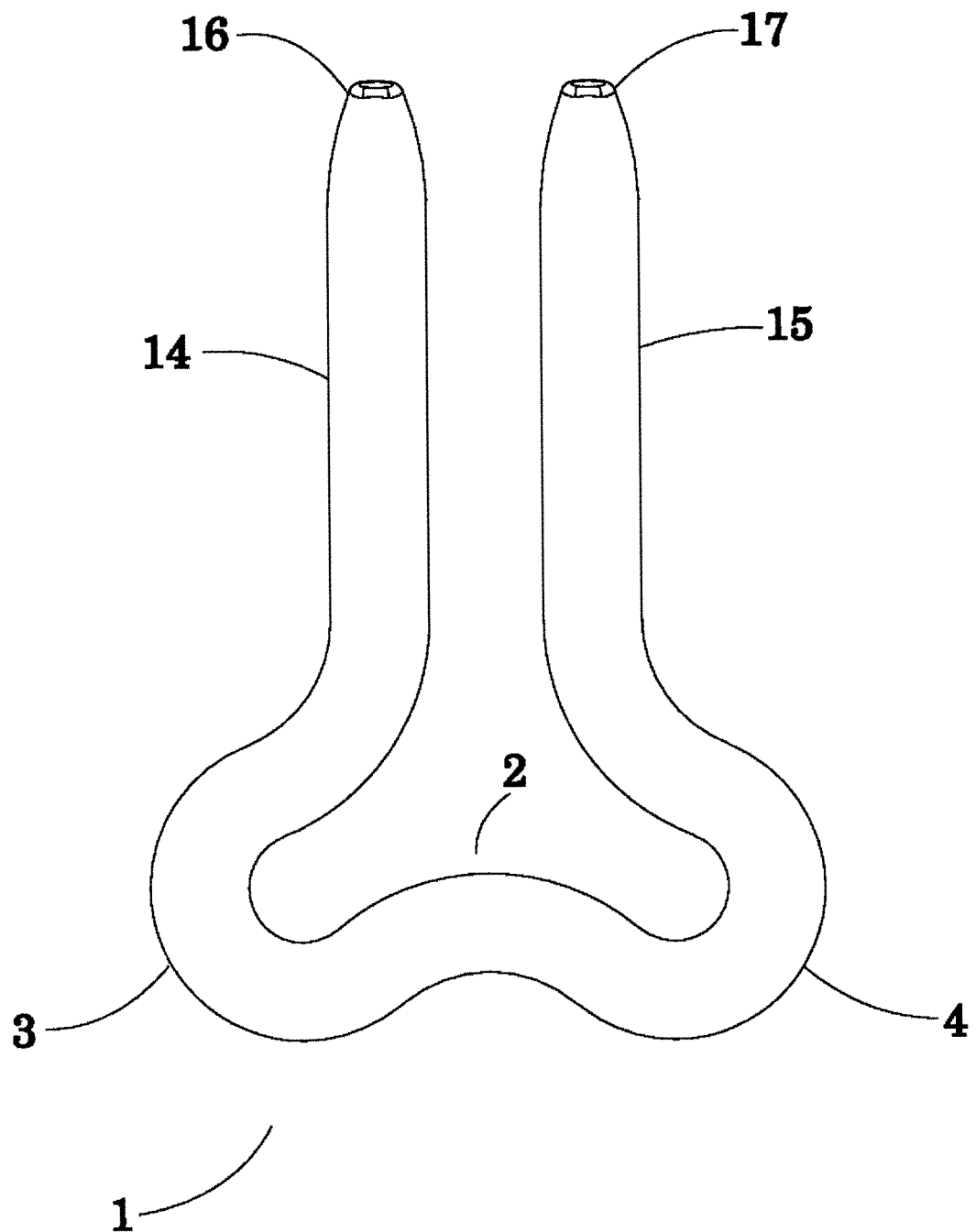
FIG. 5 illustrates a top perspective view of an individual clip with a dual prong configuration.

As shown in FIG. 5, in another embodiment of the present invention, the suture attachment clip 1 comprises a head 2 suitably shaped to allow the passage of a suture during the attachment of soft tissue to bone. In this embodiment, the head 2 preferably has a first and second lobe 3 and 4. In a preferred embodiment of the present invention, the first and second lobes 3 and 4 are symmetrical with respect to one another. In a preferred embodiment of the present invention, first and second lobes 3 and 4 are continuous with first and second bendable prongs 14 and 15. In a preferred embodiment of the present invention, the first bendable prong 14 is parallel to the second parallel prong 15. In a preferred embodiment of the present invention, first bendable prong 14 is continuous with first terminating end 16, and second bendable prongs 15 is continuous with second terminating end 17.

Figure 6:
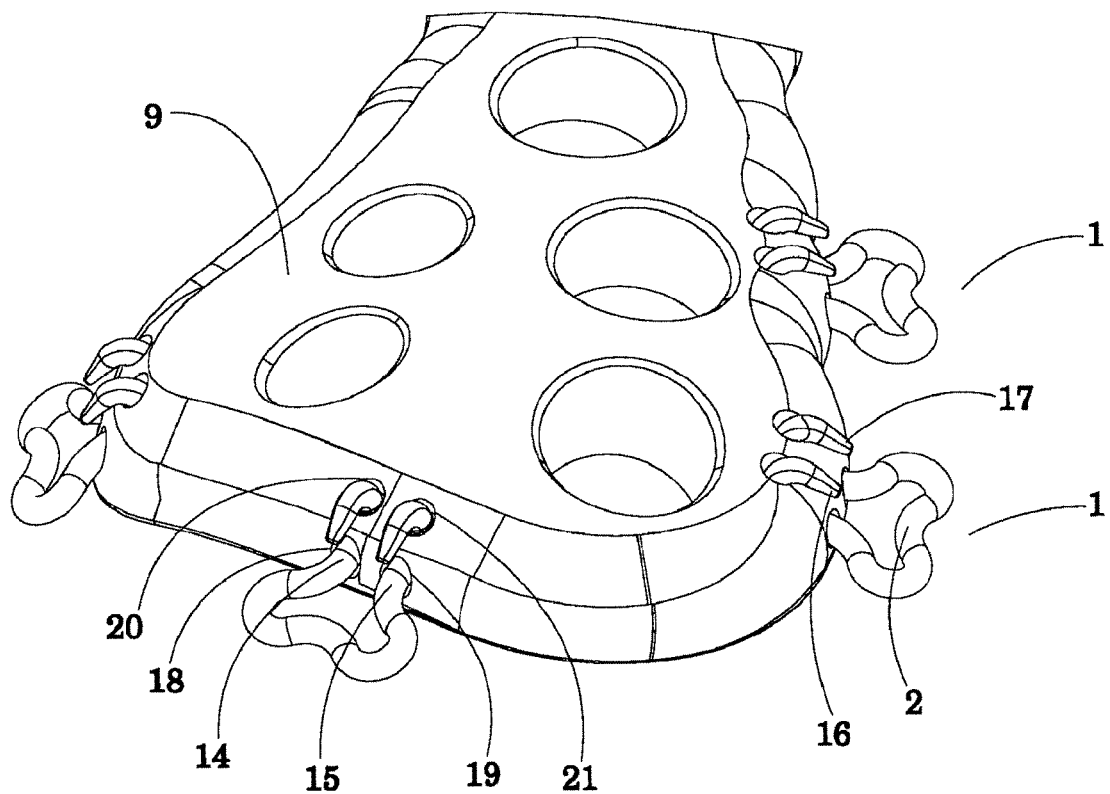
FIG. 6 illustrates a plurality of individual clips with bendable prong configurations attached to a bone plate.

As shown in FIG. 6, in the bendable prong configuration of the present invention, a plurality of individual clips 1 are attached to a bone plate 9 by inserting bendable prongs 14 and 15 of each respective clip 1 through corresponding first and second receiving orifices 18 and 19 in the bone plate. Receiving orifices 18 and 19 are preferably located on the edge of bone plate 9. In this embodiment, bendable prongs 14 and 15 are bent through corresponding first and second exit orifices 20 and 21 on the bone plate 9. Exit orifices 20 and 21 are preferably located on the edge of bone plate 9. As shown in FIG. 6, when bendable prongs 14 and 15 are bent through exit orifices 20 and 21, first and second terminating ends 16 and 17 face away from the bone plate 9 and toward the head 2 of the clip 1, thus securing the clip 1 to the bone plate 5. In this embodiment, clip 1 can be designed and manufactured specifically to fit an existing bone plate's orifices, or alternatively, the bone plate and one or more clips can be simultaneously and compatibly designed and manufactured. One or more clips 1 can be attached to the bone plate at the time of manufacture or at the time of the actual surgery.

Figure 7:
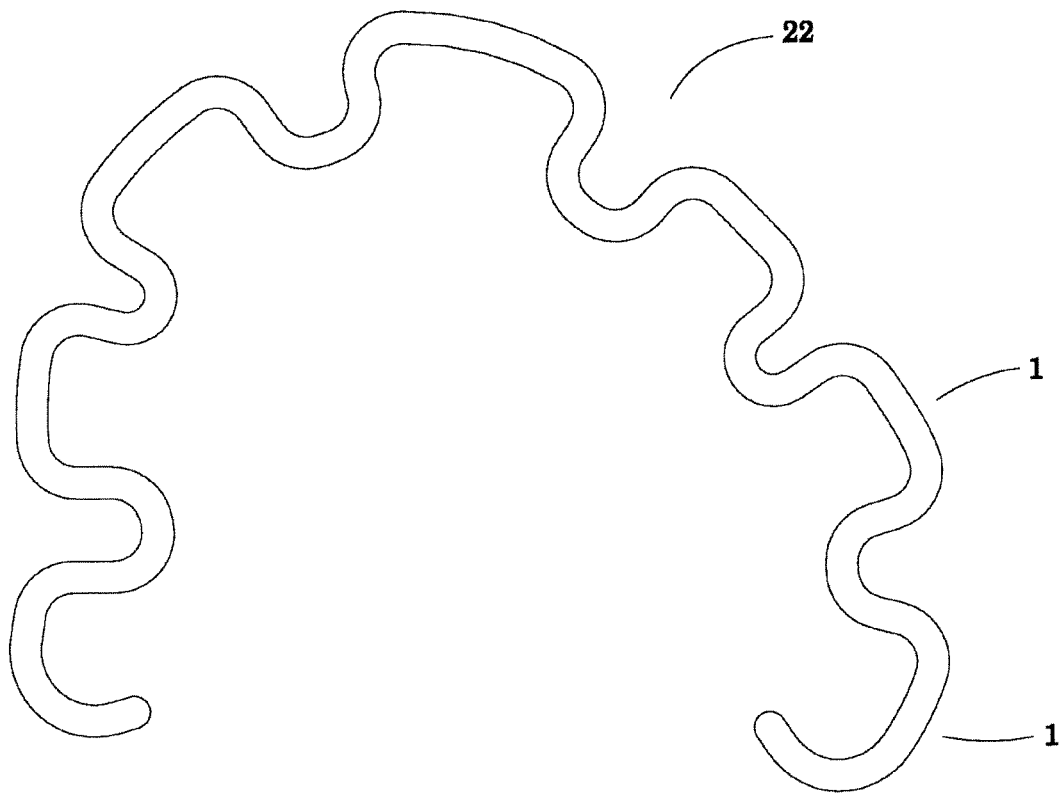
FIG. 7 illustrates a top perspective view of a multi-clip assembly.
Figure 8:
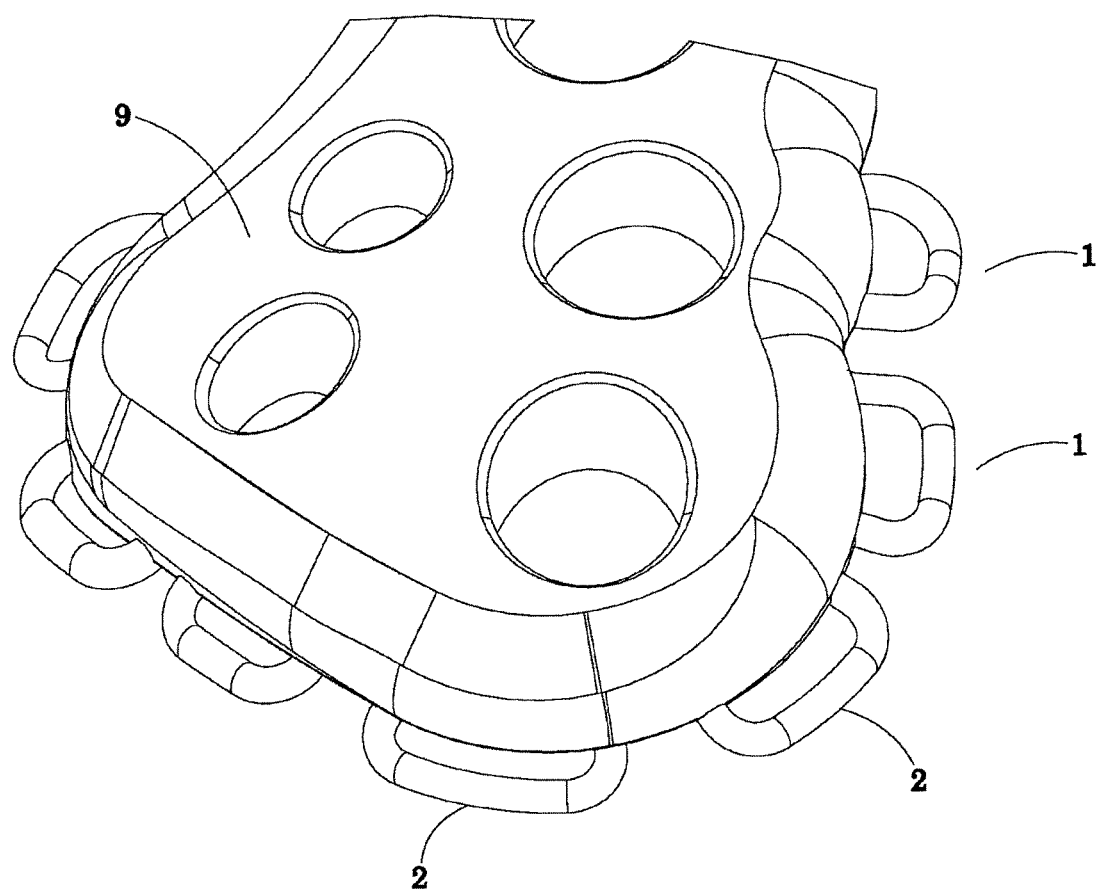
FIG. 8 illustrates a top perspective view of a bone plate with the multi-clip assembly attached to the underside of the bone plate.
Figure 9:
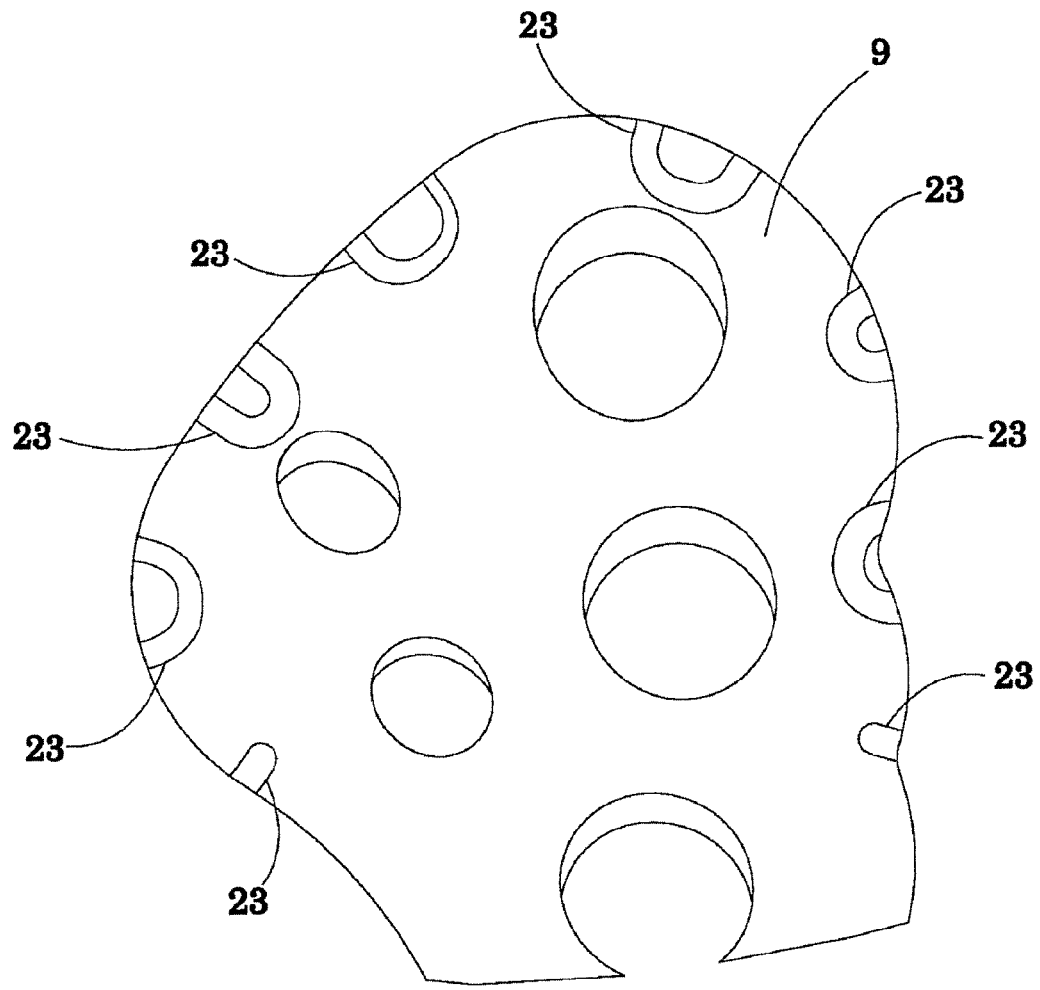
FIG. 9 illustrates a bottom view of a bone plate with a receiving channel for the multi-clip assembly.

As shown in FIG. 7, in yet another embodiment of the present invention, at least one terminal end of each clip 1, as depicted in FIG. 1, is continuous with the terminal end of an adjacent clip. The process can be repeated to form a plurality of linked clips, or a multi-clip assembly 22. Each clip 1 has a head suitably shaped to allow the passage of a suture during the attachment of soft tissue to bone. As shown in FIGS. 8 and 9, the multi-clip assembly 22 can preferably attach to the bone plate 9 by snapping the multi-clip assembly to corresponding receiving channels 23 on the bone plate 9. The receiving channels 23 are preferably located on the undersurface of the bone plate 9. While any portion of the multi-clip assembly can interlock with the corresponding receiving channels 23, as shown in FIG. 8, in a preferred embodiment of the present invention, a portion of the head 2 of each clip 1 linked together in the multi-clip assembly 22 should remain sufficiently exposed beyond the edge of the bone plate 9 in order to allow for the passage of a suture.

To further secure the multi-clip assembly 22 to the bone plate 9, the multi-clip assembly could alternatively be fastened to the bone plate by locking screws or fasteners. Depending on the fastening method used, the multi-clip assembly can be attached to the bone plate at the time of manufacture or at the time of the actual surgery.

Figure 10:
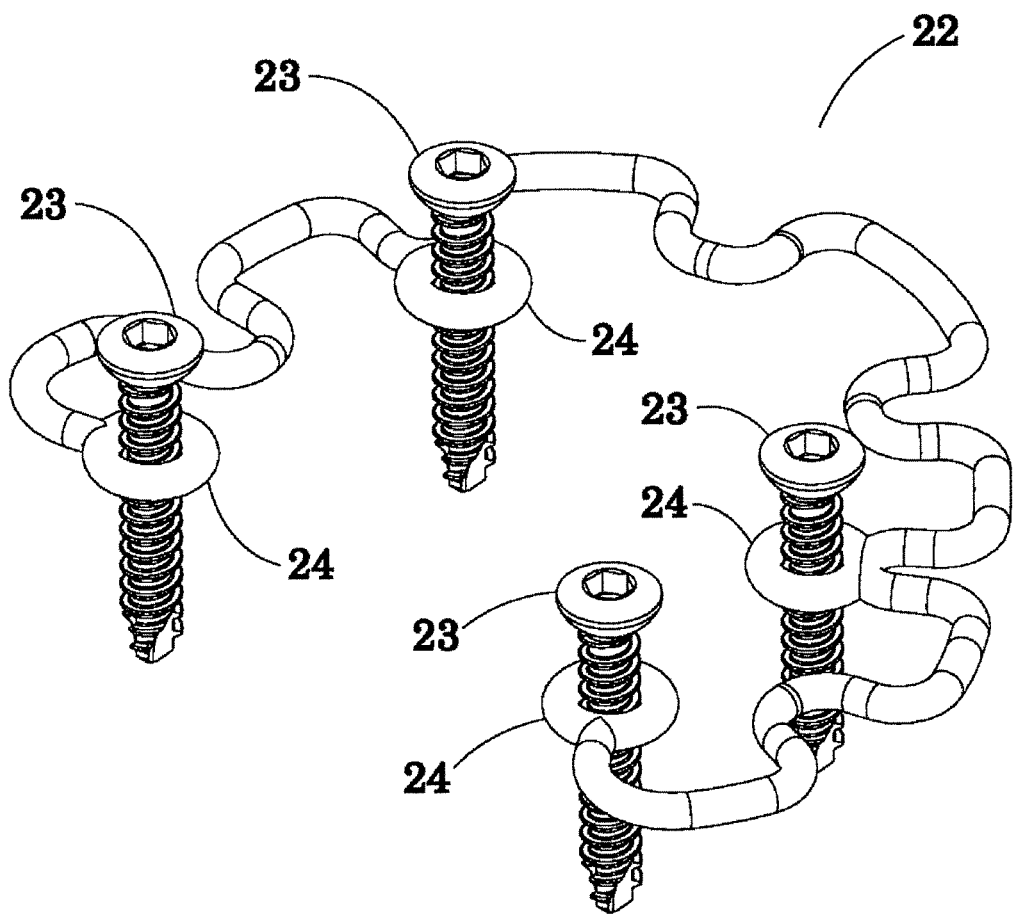
FIG. 10 illustrates a perspective view of the multi-clip assembly with eyelets and bone screws for attachment without a bone plate.

As shown in FIG. 10, the multi-clip assembly 22 can also be used without a bone plate. In this embodiment of the present invention, the multi-clip assembly 22 is fastened to the bone by inserting standard bone screws 23 or fasteners through a plurality of eyelets 24 positioned at various points on the multi-clip assembly 22, preferably at the juncture of the respective terminal ends of each linked individual clip 1 within the multi-clip assembly 22.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

I claim:

1. A system for attaching soft tissue to bone, said system comprising:
    a bone plate having a perimeter, a lower surface for placement against the bone, an upper surface opposite said lower surface, at least two holes extending through said bone plate from said upper surface to said lower surface, and at least one threaded orifice formed in said bone plate on a perimeter of said bone plate, said at least one threaded orifice adapted to receive at least a portion of a suture attachment clip;
    at least one suture attachment clip including a threaded shaft, a head portion, and a mid-longitudinal axis extending through said threaded shaft and said head portion, said threaded shaft being adapted to be received in said at least one orifice formed in said bone plate to attach said at least one suture attachment clip to said bone plate, said head portion including a first lobe portion, a second lobe portion, and a first connecting portion extending between said first and second lobe portions, wherein a maximum dimension of said threaded shaft perpendicular to the mid-longitudinal axis is less than a maximum dimension of said head portion;
    an opening formed in said head portion for receiving a suture therethrough, said opening including a first concave arcuate side corresponding to said first lobe portion, a second concave arcuate side corresponding to said second lobe portion, and a convex side corresponding to said first connecting portion, said first and second concave arcuate portions extending around more than 180 degrees; and
    a perimeter of said head portion in a first plane extending through the mid-longitudinal axis, said first lobe portion, said second lobe portion, and said first connecting portion, said perimeter having a first convex arcuate side corresponding to said first lobe portion, a second convex arcuate side corresponding to said second lobe portion, and a concave side corresponding to said first connecting portion, said first and second convex arcuate sides extending around more than 180 degrees.

2. The system of claim 1, wherein said at least one suture attachment clip further comprises a second connecting portion and a third connecting portion, said second connecting portion being connected to said first lobe portion and terminating in said threaded shaft, said third connecting portion being connected to said second lobe portion and terminating in said threaded shaft.

3. The system of claim 1, wherein said first lobe portion and said second lobe portion are symmetrical to one another about a second plane perpendicular to said first plane, said second plane extending through the mid-longitudinal axis and bisecting said first connecting portion of said head portion.

4. The system of claim 1, wherein said at least one suture attachment clip includes a maximum length along the mid-longitudinal axis, and a maximum width perpendicular to said maximum length, said maximum width of said at least one suture attachment clip being the maximum dimension of said head portion.

* * * * *